US012575767B2

(12) United States Patent
Hori et al.

(10) Patent No.: US 12,575,767 B2
(45) Date of Patent: Mar. 17, 2026

(54) OPTICAL MEASUREMENT DEVICE AND PROBE HOLDER SET

(71) Applicant: SHIMADZU CORPORATION, Kyoto (JP)

(72) Inventors: Ayaka Hori, Kyoto (JP); Shin Nakamura, Kyoto (JP); Satoshi Yomota, Kyoto (JP); Nobuyuki Akinaga, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 963 days.

(21) Appl. No.: 17/610,644

(22) PCT Filed: Dec. 23, 2019

(86) PCT No.: PCT/JP2019/050258
§ 371 (c)(1),
(2) Date: Nov. 11, 2021

(87) PCT Pub. No.: WO2020/255456
PCT Pub. Date: Dec. 24, 2020

(65) Prior Publication Data
US 2022/0218245 A1      Jul. 14, 2022

(30) Foreign Application Priority Data

Jun. 17, 2019      (JP) ................................. 2019-111848

(51) Int. Cl.
*A61B 5/1455*          (2006.01)
*A61B 5/00*            (2006.01)
(52) U.S. Cl.
CPC ........ *A61B 5/14553* (2013.01); *A61B 5/0042* (2013.01); *A61B 5/0059* (2013.01); *A61B 5/6814* (2013.01)

(58) Field of Classification Search
CPC . A61B 5/14553; A61B 5/0042; A61B 5/0059; A61B 5/6814; A61B 10/00
See application file for complete search history.

(56) References Cited

U.S. PATENT DOCUMENTS 8,244,326 B2 * 8/2012 Ninomiya .......... A61B 5/14553
                                                    600/323
9,579,061 B2    2/2017 Udagawa et al.
(Continued)

FOREIGN PATENT DOCUMENTS

JP          5610065 B2      9/2014
JP     2021145689 A  *  9/2021

OTHER PUBLICATIONS

Written Opinion by the International Search Authority for corresponding PCT application No. PCT/JP2019/050258, dated Mar. 3, 2020, submitted with a machine translation.

*Primary Examiner* — Jacqueline Cheng
*Assistant Examiner* — Tho Q Tran
(74) *Attorney, Agent, or Firm* — Muir Patent Law, PLLC

(57)                    ABSTRACT

A probe unit (30) of this optical measurement device (100) includes a base member (31) rotatable about a central axis (80), a light-transmitting probe (32) and a light-receiving probe (33) protruding in a first direction from the base member, and a plurality of pin members (34) for parting hairs, the plurality of pin members protruding in the first direction from the base member. The plurality of pin members is inclined obliquely at least either in a direction toward a central axis side of the base member or in a circumferential direction about the central axis of the base member.

13 Claims, 7 Drawing Sheets

(56)　　　　　References Cited

U.S. PATENT DOCUMENTS

| | | | | |
|---|---|---|---|---|
| 11,622,709 | B2 * | 4/2023 | Gunasekar | A61N 1/0534 |
| | | | | 600/383 |
| 2006/0184047 | A1 * | 8/2006 | Yamashita | A61B 5/6814 |
| | | | | 600/476 |
| 2015/0223694 | A1 * | 8/2015 | Funane | A61B 5/0042 |
| | | | | 600/407 |
| 2018/0348863 | A1 * | 12/2018 | Aimone | G06F 3/016 |
| 2018/0353096 | A1 * | 12/2018 | Mercier | A61B 5/6835 |
| 2019/0239807 | A1 * | 8/2019 | Watson | A61B 5/0006 |
| 2019/0328261 | A1 * | 10/2019 | Shakour | A61N 1/322 |
| 2022/0233124 | A1 * | 7/2022 | Connor | G06F 3/015 |
| 2023/0346284 | A1 * | 11/2023 | Connor | A61B 5/6803 |

* cited by examiner 500-500 cross-section

600–600 cross-section

OPTICAL MEASUREMENT DEVICE AND PROBE HOLDER SET

TECHNICAL FIELD

The present invention relates to an optical measurement device and a probe holder set. In particular, the present invention relates to an optical measurement device in which a light-transmitting probe and a light-receiving probe are placed on a head of a subject, and also relates to a probe holder set for use in such an optical measurement device.

BACKGROUND OF THE INVENTION

Conventionally, in an optical measurement device, a configuration is known in which hairs of a subject are parted when placing a light-transmitting probe and a light-receiving probe on the head of the subject. Such a configuration is disclosed, for example, in Japanese Patent No. 5610065.

Japanese Patent No. 5610065 discloses a brain function measurement device provided with a photobiological measurement holder to be mounted on a head of a subject, a light-transmitting probe, a light-receiving probe, and a light-transmitting/light-receiving control unit. The photobiological measurement holder is provided with one straight trunk, four straight first branches, one straight second branch, and a band for securing the photobiological measurement holder to the head. The trunk extends in an X-direction. The first branch extends in a Y-direction perpendicular to the X-direction and includes one end connected to the trunk and the other end tapered for parting hairs. The first branches include two branches arranged on the right side and two branches arranged on the left side with respect to the center of the trunk. The second branch extends in the Y-direction perpendicular to the X-direction and includes one end connected to the trunk and the other end tapered to part hairs. The second branch is connected to the central portion of the trunk. A through-hole is formed in each first branch. A light-transmitting probe or a light-receiving probe is configured to be inserted into the through-hole.

When placing the light-transmitting probe and the light-receiving probe, first, a subject, a doctor, or the like inserts the light-transmitting probe and the light-receiving probe into the through-holes. Next, the subject, the doctor, or the like places the photobiological measurement holder on the head in such a manner as to move the holder from the front of the head toward the rear of the head while parting hairs. Then, the holder is fixed to the head.

PRIOR ART DOCUMENT

Patent Document

Patent Document 1: Japanese Patent No. 5610065

SUMMARY OF THE INVENTION

Problems to be Solved by the Invention

As disclosed in the above-described Japanese Patent No. 5,610,065, in order to perform accurate measurement when performing optical measurement (cerebral function measurement) of a head of a subject, it is crucial to bring the tip of the probe in close contact with the head surface such that hairs are not interposed between the probe and the head surface (scalp).

In the above-described Japanese Patent No. 5610065, a comb-shaped photobiological measurement holder having the first branches and the second branch is used such that the mounting of the photobiological measurement holder can be performed while parting hairs by the first branches and the second branch. However, even in the photobiological measurement holder having such a configuration, in some cases, hairs may be interposed between the probe and the head surface.

In a case where hairs are interposed therebetween, it is required for a doctor or the like to remove the probe once from the through-hole and reinsert the probe into the through-hole via the through-hole in a state in which the doctor or the like has parted hairs with a rod-shaped tool to expose the head surface. For this reason, conventionally, in addition to the subject, an assistant, such as, e.g., a doctor, is required to assist the attachment of the probe when performing the cerebral function measurement. Further, the operation for parting hairs is troublesome because it is required to be performed through each of the narrow through-holes by using a rod-shaped tool.

Under the circumstances, it has been desired that a probe can be placed such that hairs are not interposed between the probe and the head surface only by a subject without requiring an assistant and that the operation of parting hairs can be performed simply.

The present invention has been made to solve the above-described problems. One object of the present invention is to provide an optical measurement device and a probe holder set capable of arranging a probe such that hairs are not interposed between the probe and a head surface only by a subject in a simple operation.

Means for Solving the Problem

In order to achieve the above-described object, as a result of extensive studies by the present inventors, it has been found that the reason that hairs are interposed between the probe and the head surface by a conventional method is especially largely affected by the following two points. First, in a case where hairs extend along a head surface (i.e., hairs are laying) rather than a case where hairs extend upward from the head surface, a space is hardly formed between hairs and the head surface even if the hairs are parted. For this reason, it is difficult to form a space for bringing the probe in close contact with the head surface. Second, in some cases, it may not be effective to pair the hairs linearly in a particular direction because the direction in which hairs extend (the direction of hair orientation) differs depending on the measurement position of the head and/or the personal difference of a subject. For example, even if hairs are parted in a direction parallel to the hairs, the hairs cannot be paired so as to expose the region for arranging the probe.

Based on the above-described findings, the inventors of the present application have conceived the following invention. That is, an optical measurement device according to a first aspect of the present invention includes:

a device main body configured to irradiate a head surface of a subject with measurement light via a light-transmitting probe and detect the measurement light emitted from the head surface by way of an inside of a head via a light-receiving probe;

a holder configured to be attached to the head of the subject; and a probe unit held by the holder, wherein the probe unit includes:

a base member rotatably held by the holder about a central axis;

the light-transmitting probe protruding from the base member in a first direction toward the head surface;

the light-receiving probe protruding from the base member in the first direction; and a plurality of pin members each protruding from the base member in the first direction for parting hairs of the head surface, wherein the plurality of pin members is inclined obliquely at least either in a direction toward a central axis side of the base member or in a circumferential direction about the central axis.

A probe holder set for an optical measurement device configured to irradiate a head surface of a subject with measurement light via a light-transmitting probe and detect the measurement light emitted from the head surface by way of an inside of the head via a light-receiving prove, according to a second aspect of the present invention, the probe holder set includes:

a holder configured to be attached to the head of the subject; and a probe unit held by the holder, wherein the probe unit includes:

a base member rotatably held by the holder about a central axis:

the light-transmitting probe protruding from the base member in a first direction toward the head surface;

the light-receiving probe protruding from the base member in the first direction; and a plurality of pin members each protruding from the base member in the first direction for parting hairs of the head surface, and wherein the plurality of pin members is inclined obliquely at least either in a direction toward a central axis side of the base member or in a circumferential direction about the central axis.

Note that in this specification, the term "pin member" includes a broad concept meaning an elongated rod-shaped member and does not mean a member for fixing or sewing an object.

Effects of the Invention

According to the present invention, as described above, the probe unit includes a plurality of pin members protruding from the base member rotatably held by the holder about a central axis in the first direction for parting hairs of the head surface. Therefore, by simply placing the probe unit on the head surface and rotates it by the subject himself/herself, it is possible to rotate the pin members to part the hairs. At this time, the pin members are inclined obliquely at least either in a direction toward the central axis side or in a circumferential direction. For this reason, even in a case where hairs extend along the head surface, it is possible to lift the hairs along the slope of the pin member while parting the hairs. As a result, the parted hairs are raised, and therefore a space capable of arranging the probe without interposing hairs can be formed in the vicinity of the head surface. Further, the traveling path of the pin member is a closed circumference path about the central axis. Therefore, even if hairs extend in any orientation, the hairs can be parted by the pin members. As a result, according to the above-described configuration, it is possible to arrange the probe such that hairs are not interposed between the probe and the head surface by only a subject in a simple operation.

EMBODIMENTS FOR CARRYING OUT THE INVENTION

Figure 1:
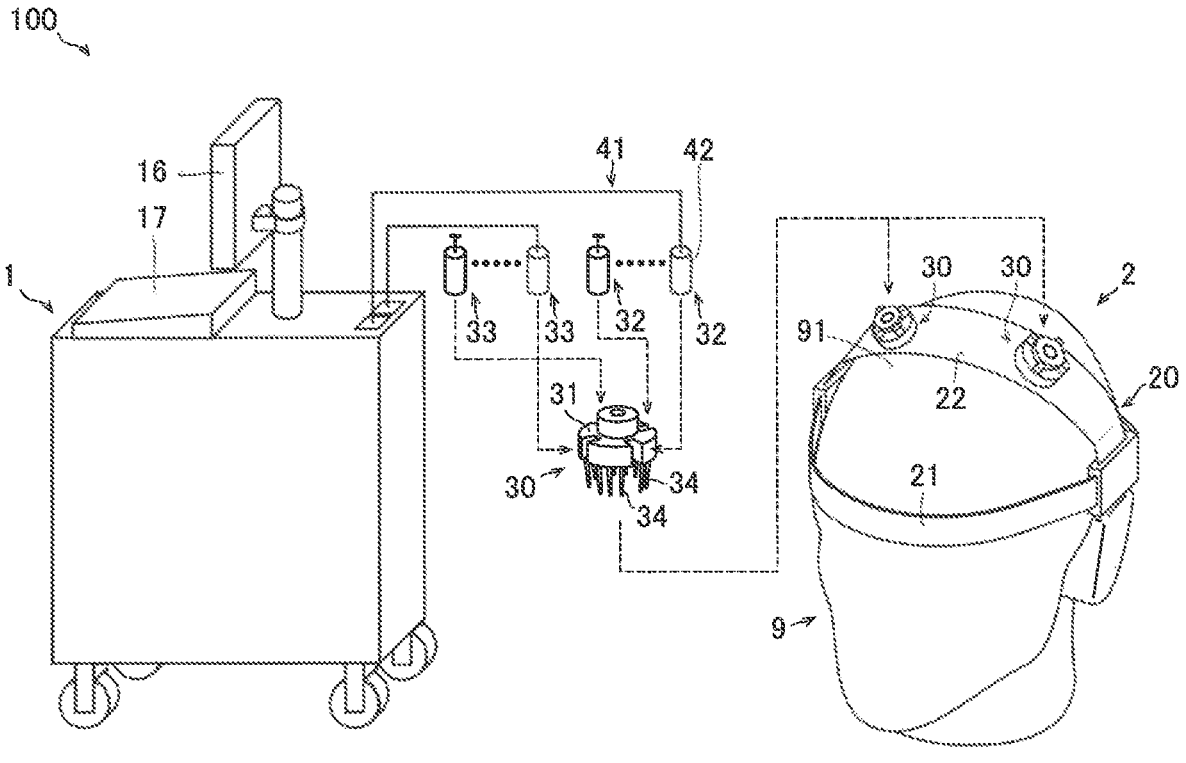
FIG. 1 is a schematic perspective view showing an optical measurement device and a probe holder set according to one embodiment.

Hereinafter, some embodiments in which the present invention is embodied will be described with reference to the attached drawings.

First, with reference to FIGS. 1 to 8, the entire configuration of an optical measurement device 100 according to one embodiment will be described. The optical measurement device 100 is configured to irradiate a head surface 91 of a subject 9 with measurement light and detect the measurement light emitted from the head surface 91 via the inside of the head. The optical measurement device 100 is a device configured to measure the change in the cerebral blood flow that reflects the brain activities of the subject 9, based on the intensity (amount of the received light) of the detected measurement light.

The optical measurement device 100 is provided with a device main body 1 and a probe holder set 2. The probe holder set 2 includes a holder 20 and a probe unit 30.

Further, the optical measurement device 100 is provided with a plurality of measurement probes (light-transmitting probes 32 and light-receiving probes 33) connected to the device main body 1.

Figure 2:
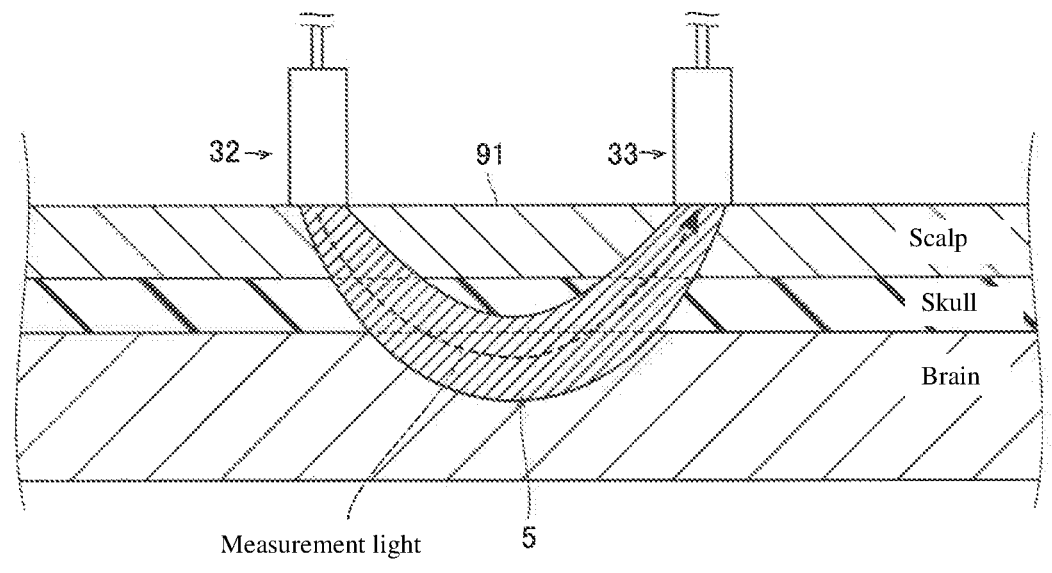
FIG. 2 is a schematic view for explaining optical measurement by a light-transmitting probe and a light-receiving probe.

The plurality of measurement probes each function as a light-transmitting probe 32 or a light-receiving probe 33, and both the light-transmitting probe 32 and the light-receiving probe 33 have the same structure. The measurement probe means a probe to be brought into contact with or inserted into a sample for the purpose of measurement, experiments, etc. The measurement probe has one end connected to the device main body 1 and the other end to be brought into contact with the head surface 91 of the subject 9. As shown in FIG. 2, the device main body 1 emits measurement light in the near-infrared range from the light-transmitting probe 32 arranged on the head surface 91 of the subject 9. Then, the device main body 1 detects the measurement light incident from the light-receiving probe 33 arranged on the head surface 91. The region serving as the path of the measurement light between one light-transmitting probe 32 and one light-receiving probe 33 configures one measurement point (measurement channel 5). The wavelength region of the near-infrared light is, for example, 700 nm or more and 900 nm or less. The near-infrared light is less absorptive in vivo, and therefore, the measurement light can reach the cerebral region in the head.

When the amount of hemoglobin in the blood in the brain increases at the activation site reflecting the brain activities of the subject 9, the amount of measurement light absorbed by the hemoglobin increases. Thus, it is possible to acquire the change in the hemoglobin content associated with the cerebral activities based on the intensity of the acquired measurement light. Note that hemoglobin is classified into oxyhemoglobin bound to oxygen and deoxyhemoglobin not bound to oxygen. Oxyhemoglobin and deoxyhemoglobin have different absorption characteristics. For this reason, the optical measurement device 100 performs measurement using the measurement light of a plurality of wavelengths (e.g., three wavelengths of 780 nm, 805 nm, and 830 nm) considering the difference in the absorption characteristics. The temporal changes in the amounts of hemoglobin and the total amount thereof are calculated based on the intensities of measurement light of the respective acquired wavelengths.

As a result, based on the intensity (amount of the received light) of the measurement light incident on the light-receiving probe 33, it is possible to acquire the change in the amount of hemoglobin associated with cerebral activities, i.e., the change in the blood flow rate or the activation state of oxygen metabolism in a non-invasive manner. The optical measurement device 100 is provided with a plurality of light-transmitting probes 32 and a plurality of light-receiving probes 33. By measuring brain regions at a plurality of points (a plurality of measurement channels 5) using a plurality of light-transmitting probes 32 and a plurality of light-receiving probes 33, it is possible to acquire the two-dimensional distribution of which regions of the brain are active and how.

Returning to FIG. 1, the probe unit 30 holds the light-transmitting probe 32 and the light-receiving probe 33 each connected to the device main body 1. The probe unit 30 is arranged on the head surface 91 of the subject 9 and is configured to maintain the relative position between the light-transmitting probe 32 and light-receiving probe 33, which constitute the measurement channel 5 by the measurement light, constant.

Specifically, the probe unit 30 includes a base member 31, a light-transmitting probe 32, a light-receiving probe 33, and a plurality of pin members 34 for parting hairs on the head surface 91. The light-transmitting probe 32, the light-receiving probe 33, and the plurality of pin members 34 are provided to the base member 31.

The probe unit 30 is held by the holder 20. The probe unit 30 is held in place on the head surface 91 of the subject 9 by the holder 20. In this embodiment, the probe unit 30 is held by the holder 20 in such a manner as to be rotatable about the central axis. The probe unit 30 is configured such that the plurality of pin members 34 can part hairs by being rotated about the central axis with the probe unit 30 arranged on the head surface 91. The detailed configuration of the probe unit 30 will be described later.

The holder 20 is mounted on the head of the subject 9. The holder 20 is configured to hold one or a plurality of probe units 30. The holder 20 has, for example, a socket (not shown) capable of removably mounting the probe unit 30 and removably and rotatably holds the probe unit 30 about the central axis. The holder 20 may, for example, hold the probe unit 30 in a rotatable manner but in a non-separably connected manner.

The holder 20 is not particularly limited in shape as long as it can be mounted immovably on the head of the subject 9. The holder 20 may have a variety of shapes. For example, it is possible to adopt a holder shape, such as, e.g., a headband-like shape surrounding a head in a circumferential direction, a headphone shape to be mounted with both ears covered, a headgear-like shape that covers a part of a head, and a helmet-like shape that entirely covers a head.

In the example shown in FIG. 1, the holder 20 includes a band portion 21 that surrounds the head from the forehead to the back of the head in the circumferential direction and an arch portion 22 that extends laterally in the right-left direction from the left ear via the the upper portion of the head to the right ear. The band portion 21 includes, for example, a stretchable material and is secured to the head by the shrinkage force. The arch portion 22 is provided with a socket or a bracket having a through-hole and is configured to mount the probe unit 30 to the socket or the bracket. The holder 20 of the example shown in FIG. 1 is configured to hold the probe units 30 one on the left side and the other on the right side bordering the midline of the head. The holder 20 of the example shown in FIG. 1 can hold, for example, two left probe units 30 and two right prove units 30 in the vicinity the positions of C3 and C4 according to the International 10/20 method. The number and the position for holding the probe units 30 by the holder 20 are not particularly limited and are not limited to those shown in FIG. 1.
(Device Main Body)

Figure 3:
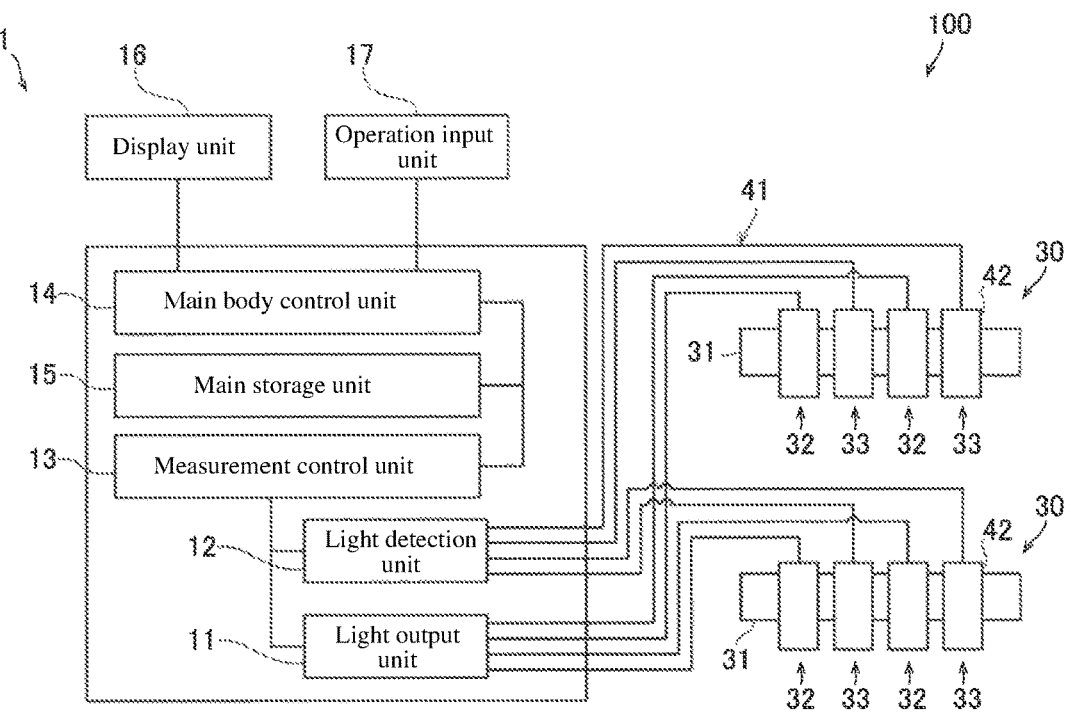
FIG. 3 is a block diagram showing a configuration of an optical measurement device according to one embodiment.

As shown in FIG. 3, the device main body 1 is provided with a light output unit 11 and a light detection unit 12.

The light output unit 11 outputs measurement light to the light-transmitting probes 32. The light output unit 11 is provided with, for example, a semiconductor laser as a light source. To the light output unit 11, a plurality of light-transmitting probes 32 can be connected. The light output unit 11 can individually output measurement light at any timing to each connected light-transmitting probe 32.

The light detection unit 12 detects measurement light incident on the light-receiving probe 33. The light detection unit 12 is provided with, for example, a photomultiplier tube or a photodiode as a detector. To the light detection unit 12, a plurality of light-receiving probes 33 can be connected. The light detection unit 12 can individually detect the measurement light from each connected light-receiving probe 33.

The device main body 1 can connect up to N pieces of the light-transmitting probes 32 and up to M pieces of the light-receiving probes 33. The total number of the connectable probes is N+M, where N and M are each a natural number equal to or greater than 2.

Further, the device main body 1 is provided with a measurement control unit 13, a main body control unit 14, and a main storage unit 15. The measurement control unit 13 performs the operation control of the light output unit 11 and the light detection unit 12, such as, e.g., the timing control of the light output and the light detection. The measurement control unit 13 includes a driver circuit of the light output unit 11 and the light detection unit 12. The main body control unit 14 executes various programs to control the entire device main body 1. The main body control unit 14 is configured by a computer including a processor and a memory. The main storage unit 15 is configured to store various programs to be executed by the main body control unit 14 and measurement data obtained as a result of measurement. The main storage unit 15 is configured by a non-volatile memory, such as, e.g., a hard disk drive. Further, the optical measurement device 100 is provided with a display unit 16 and an operation input unit 17 connected to the device main body 1. The display unit 16 is, for example, a liquid crystal display. The operation input unit 17 includes an input device, such as, e.g., a keyboard and a mouse.

The optical measurement is initiated by, for example, an input operation via the operation input unit 17. The main body control unit 14 that has received the input operation performs the control for starting the measurement. When the measurement is started, the measurement control unit 13 controls the light output unit 11 in such a manner that each of the light-transmitting probes 32 outputs measurement light in order at a predetermined cycle. Then, in synchronization with the output of the measurement light, the measurement control unit 13 controls the light detection unit 12 to detect the measurement light from the light-receiving probe 33 that configures the measurement channel 5 together with the light-transmitting probe 32 from which the measurement light has been output. Based on the detected signal, the main body control unit 14 analyzes the change in the hemoglobin content associated with the cerebral activities and controls the display unit 16 to display the measurement result.

(Probe Unit)

Next, referring to FIGS. 1 and 4 to 8, the configuration of the probe unit 30 will be described. The probe unit 30 includes at least one light-transmitting probe 32 and at least one light-receiving probe 33.

Figure 4:
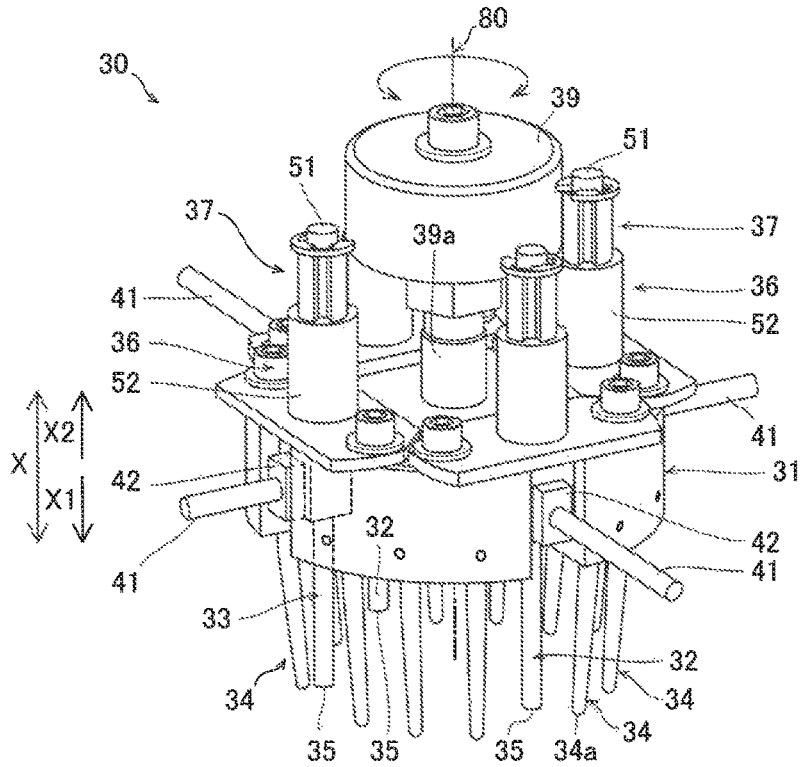
FIG. 4 is a perspective view showing one example of a probe unit.

The base member 31 holds the light-transmitting probe 32 and the light-receiving probe 33 and a plurality of pin members 34. Further, the base member 31 is held by a holder 20 rotatably about the central axis 80 (see FIG. 4). In the example shown in FIG. 1, the base member 31 is detachably provided to the holder 20 and can be removed from the holder 20. As shown in FIG. 4, the base member 31 is formed in, for example, a circular shape and is arranged to face the head surface 91. The base member 31 is configured to hold the light-transmitting probe 32 and the light-receiving probe 33 at the outer peripheral portion thereof. The central axis 80 is an axis extending toward the surface 91.

Hereinafter, with respect to the base member 31 held by the holder 20 (see FIG. 1), the first direction toward the head surface 91 side (the direction approaching the head) is denoted as an X1-direction, and the second direction toward the other side (the direction away from the head) of the head surface 91 is denoted as an X2-direction. Both the X1-direction and the X2-direction are collectively referred to as an X-direction. The X1-direction is an example of the "first direction" recited in claims, and the X2-direction is an example of the "second direction" recited in claims.

<Light-Transmitting Probe and Light-Receiving Probe>

The light-transmitting probe 32 and the light-receiving probe 33 are each provided so as to protrude from the base member 31 in the X1-direction toward the head surface 91. In the configuration example of FIG. 4, the light-transmitting probe 32 and the light-receiving probe 33 are each detachably mounted to the base member 31. In the configuration example of FIG. 4, two light-transmitting probes 32 and two light-receiving probes 33 are mounted to the base member 31.

Figure 5:
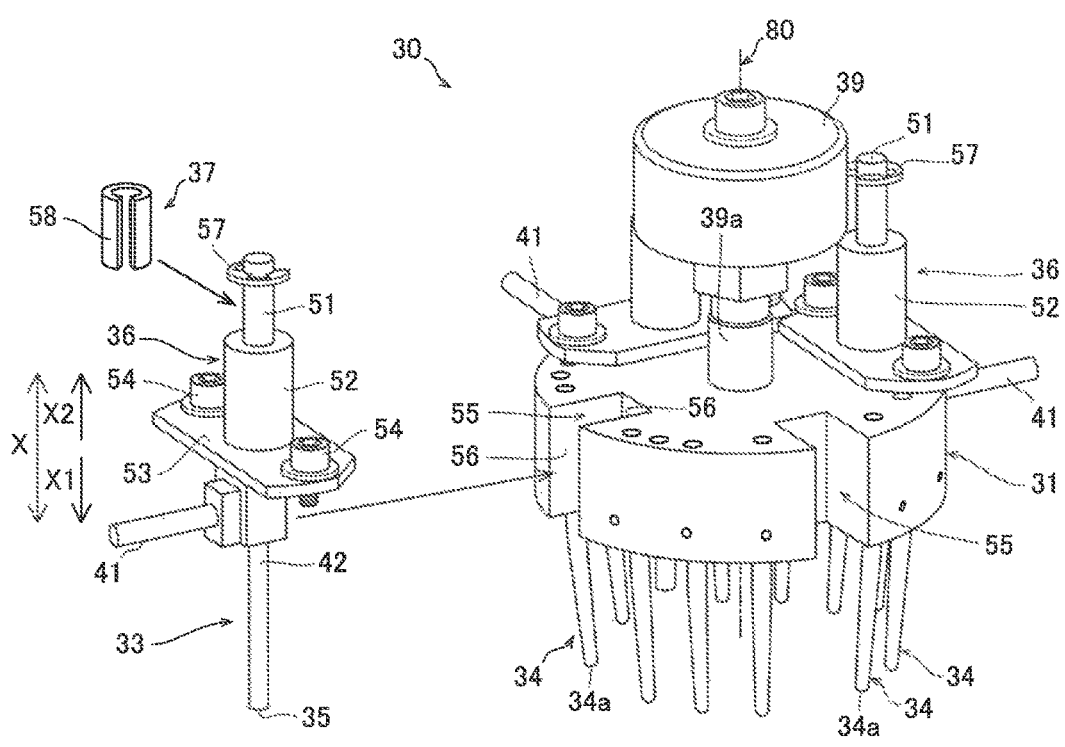
FIG. 5 is an exploded perspective view for explaining a configuration of a probe unit.

As shown in FIG. 5, the light-transmitting probe 32 and the light-receiving probe 33 each have an optical fiber cable (hereinafter referred to as "optical fiber") 41 and a fiber head 42 for holding the optical fiber 41. The fiber head 42 has a tubular structure in which the optical fiber 41 can be inserted and is configured to hold and protect the tip portion of the optical fiber 41. The optical fiber 41 is provided so as to pass through the inside of the fiber head 42 to be exposed from the tip portion of the fiber head 42. The tip portion of the fiber head 42 from which the optical fiber 41 is exposed is served as the tip 35 of the light-transmitting probe 32 or that of the light-receiving probe 33. With this, the light-transmitting probe 32 can emit measurement light from the tip 35, and the light-receiving probe 33 can cause the measurement light to be incident on the inside of the optical fiber 41 from the tip 35.

In FIG. 5, as an example, an L-shaped fiber head 42 in which the tip portion is bent substantially at a right angle is shown. The fiber head 42 has a hollow tubular structure and is attached to the base member 31 with the tip portion (i.e., the tip 35 of the probe) facing in the X1-direction. The fiber head 42 is a cylindrical member made of non-translucent resin or aluminum (aluminum or aluminum alloy). The example of the resin is exemplified by modified PPE (polyphenylene Ether), POM (polyoxymethylene), and the like. The optical fiber 41 is a light-transmitting cable in which a fiber wire constituting a light-transmitting path is covered with a covering material.

Figure 6:
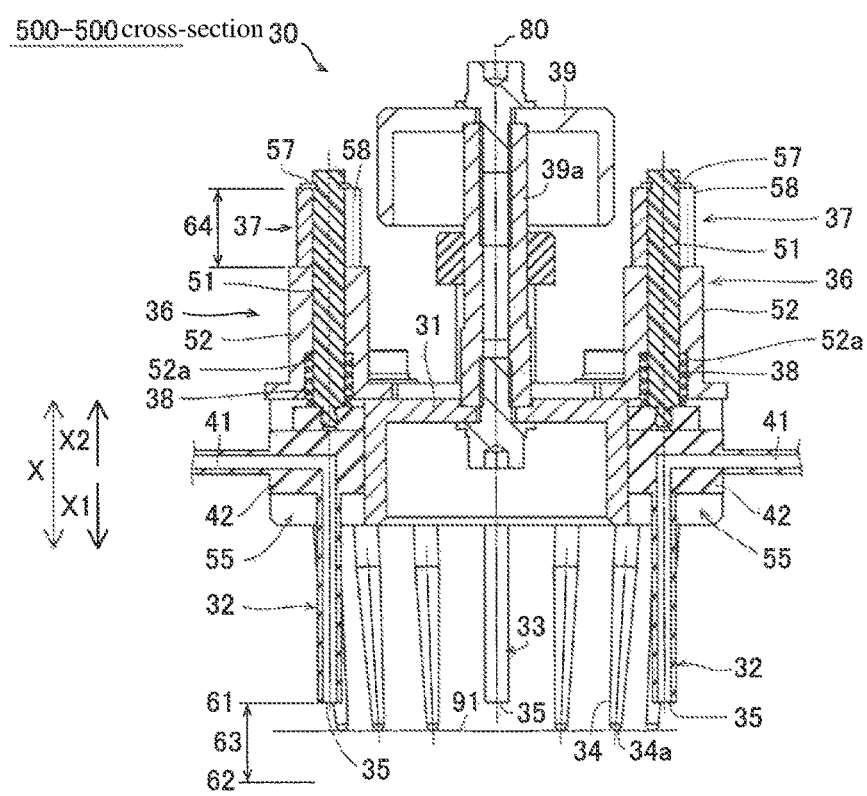
FIG. 6 is a cross-sectional view of a probe unit taken along the line 500-500 in FIG. 8.

In the configuration example of FIGS. 4 and 5, the light-transmitting probe 32 and the light-receiving probe 33 are each provided so as to be movable in the X-direction with respect to the base member 31. Specifically, the light-transmitting probe 32 and light-receiving probe 33 are each mounted to the base member 31 via a guide mechanism 36 one by one. The guide mechanism 36 includes a shaft 51 extending in the X-direction and a cylindrical guide tube 52 through which the shaft 51 is inserted. As shown in FIG. 6, the shaft 51 is connected to the end of the fiber head 42 in the X2-direction to hold the fiber head 42. The guide tube 52 slidably holds the shaft 51 in the X-direction. When the shaft 51 is moved in the X-direction, the light-transmitting probe 32 or the light-receiving probe 33 held by the shaft 51 is moved in the X-direction. Note that a stopper member 57, such as, e.g., a snap ring, is attached to the upper end portion of the shaft 51.

The guide mechanism 36 is mounted to the base member 31 with the light-transmitting probe 32 or the light-receiving probe 33 movably held in the X-direction. As shown in FIG. 5, the guide tube 52 has a flange portion 53 protruding outward on the outer peripheral portion. The flange portion 53 is placed on the top surface of the base member 31 and is removably secured to the base member 31 by fastening members 54, such as, e.g., bolts.

On the outer peripheral surface of the base member 31, arrangement portions 55 each having a notched shape capable of arranging the light-transmitting probe 32 or the light-receiving probe 33 are formed. The inner surface of the arrangement portion 55 having a notched shape is configured as flat sliding surfaces 56 extending in a first direction and a second direction. The light-transmitting probe 32 or the light-receiving probe 33 is positioned inside the arrangement portion 55 and moves along the sliding surfaces 56. The sliding surfaces 56 support the light-transmitting probe 32 or the light-receiving probe 33 against the external force applied in the circumferential direction (side surface side) when the base member 31 is rotated about the central axis 80.

With this configuration, as shown in FIG. 6, each of the light-transmitting probe 32 and the light-receiving probe 33 is provided to the base member 31 so as to be movable to a first position 61 and a second position 62. The first position 61 is a position away from the head surface 91 than the plurality of pin members 34. The second position 62 is a position closer to the head surface 91 than the plurality of pin members 34. The stroke amount 63 between the first position 61 and the second position 62 is equal to the length 64 between the stopper member 57 and the upper end of the guide tube 52 in FIG. 6. Note that the first position 61 and the second position 62 are the positions of the tip 35 of the probe.

<Lock Mechanism and Biasing Member>

In the configuration example of FIG. 6, the probe unit 30 includes a lock mechanism 37 and a biasing member 38.

The lock mechanism 37 is configured to releasably hold each of the light-transmitting probe 32 and the light-receiving probe 33 at the first position 61. The biasing member 38 is configured to bias each of the light-transmitting probe 32 and the light-receiving probe 33 toward the second position 62.

As shown in FIG. 5, the lock mechanism 37 includes a spacer 58 provided between the stopper member 57 provided at the upper end of the shaft 51 and the upper end of the guide tube 52. The spacer 58 has, for example, a C-shaped cross-section and is removably mounted to the shaft 51 (see FIG. 6). The spacer 58 has a length substantially corresponding to the length 64 described above. As shown in FIG. 6, the spacer 58 is in contact with the stopper member 57 and the upper end of the guide tube 52 in a state in which the probe is in the first position 61 so as not to move the shaft 51 in the X1-direction.

The biasing member 38 is arranged inside the guide tube 52. The biasing member 38 biases the fiber head 42 in the X1-direction. In the example of FIG. 6, the biasing member 38 is a compressed-coil spring in which the shaft 51 is provided. The upper end portion of the biasing member 38 is in contact with the locking portion 52*a* formed on the inner surface of the guide tube 52, and the lower end portion of the biasing member 38 is in contact with the upper surface of the fiber head 42. When the probe is positioned at the first position 61, the biasing member 38 is in a state in which it is compressed more than its natural length to press the probe in the X1-direction.

When the spacer 58 is detached from the shaft 51, the locking by the lock mechanism 37 is unlocked, which allows the shaft 51 to move in the X1-direction. Consequently, the biasing force of the biasing member 38 causes the probe (light-transmitting probe 32 and light-receiving probe 33) to move in the X1-direction toward the second position 62.

(Pin Member)

As shown in FIG. 4, the plurality of pin members 34 is provided so as to protrude from the base member 31 in the X1-direction. The pin member 34 is configured to be moved in the circumferential direction in accordance with the rotational movement of the base member 31 (probe unit 30) about the central axis 80 to part the hairs of the head surface 91. The pin member 34 is made of resin material (e.g., PP: polypropylene, etc.) formed in an elongated rod-shape (needle shape) suitable for parting hairs. The pin member 34 is provided so as to protrude from the lower surface of the base member 31 (X1-direction side surface) in the X1-direction. The pin member 34 is fixed to the base member 31. The tip 34*a* of the pin member 34 (X1-direction side end) has a rounded smooth surface, such as, e.g., a spherical surface.

Figure 7:
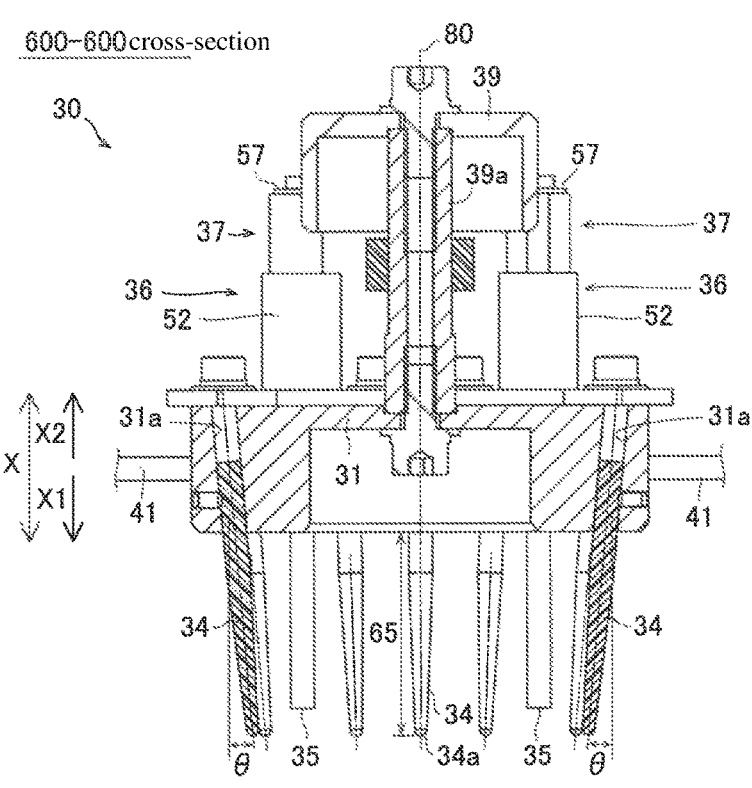
FIG. 7 is a cross-sectional view of a probe unit taken along the line 600-600 in FIG. 8.
Figure 8:
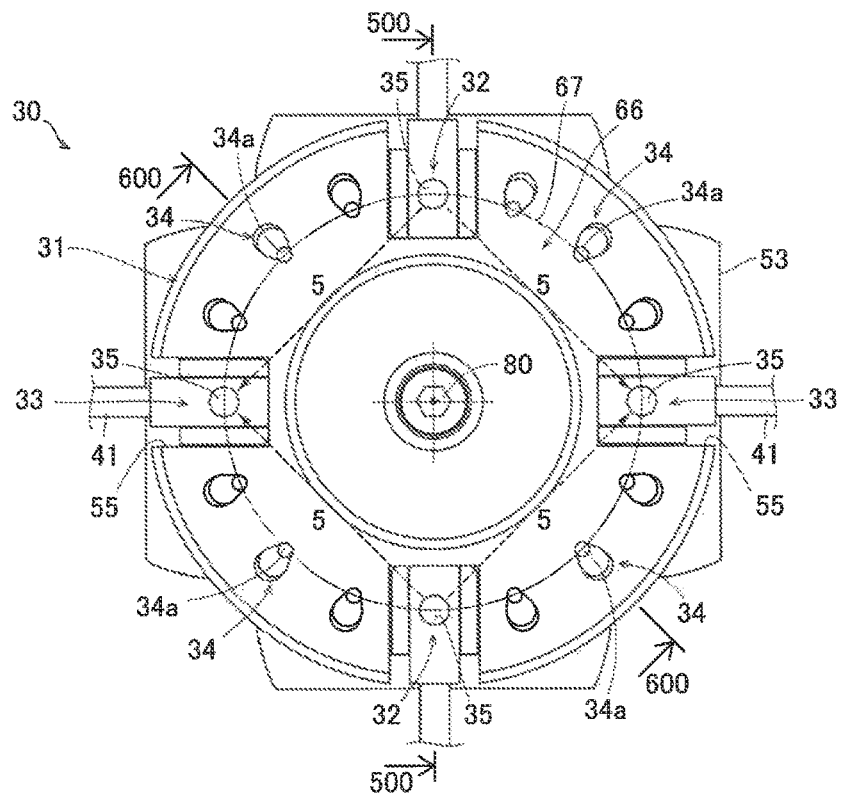
FIG. 8 is a bottom view of the probe unit shown in FIG. 4.
Figure 13:
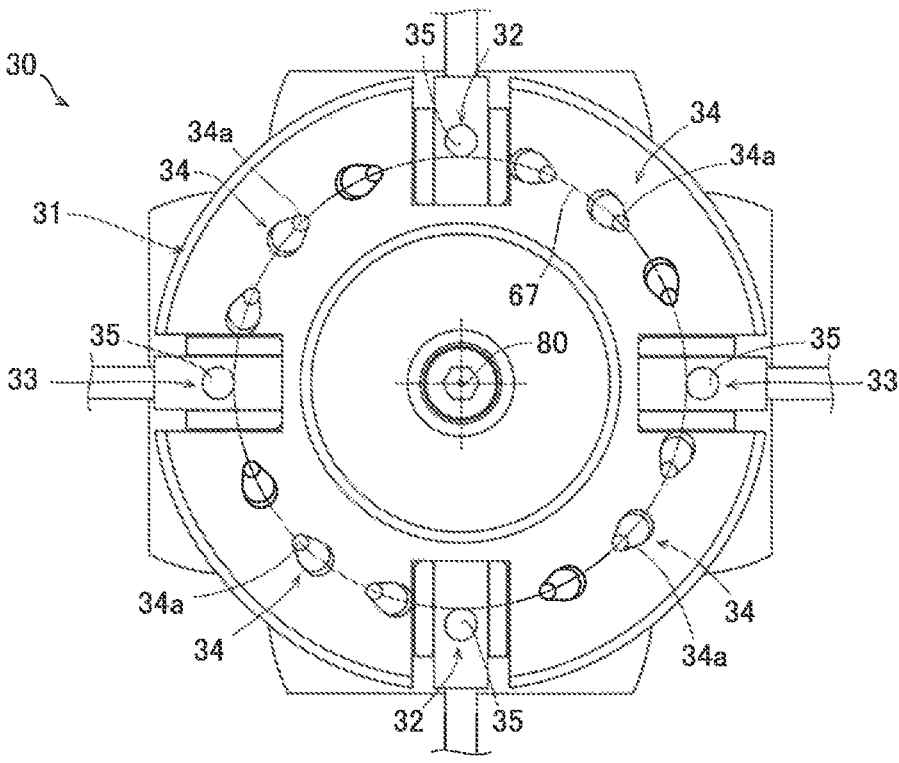
FIG. 13 is a view showing a modification in which a plurality of pin members is obliquely inclined in a circumferential direction about a central axis of a base member.

A plurality of pin members 34 is provided so as to be obliquely inclined at least either in a direction toward the central axis 80 of the base member 31 or the circumferential direction about the central axis 80. In this embodiment, as shown in FIGS. 7 and 8, the plurality of pin members 34 is inclined obliquely in a direction toward the central axis 80 of the base member 31. As shown in FIG. 13, the plurality of pin members 34 may be provided so as to be inclined obliquely in the circumferential direction about the central axis 80. The plurality of pin members 34 may be inclined both in the direction toward the central axis 80 and in the circumferential direction about the central axis 80.

In the example of FIG. 7, the inclination angle θ of the pin member 34 is, for example, 1 degree<θ<10 degrees, more specifically, 3 degrees<θ<8 degrees. FIG. 7 shows an example of θ=5 degrees. The inclination angle θ is an angle formed by the centerline of the pin member 34 passing through the tip 34*a* with respect to the central axis 80 (X-direction). In contrast, the tip 35 of the light-transmitting probe 32 and that of the light-receiving probe 33 each extend from the lower surface of the base member 31 substantially in parallel to the central axis 80.

In the example FIG. 7, the pin member 34 has a linear shape that is tapered toward the tip 34*a*. The root portion of the pin member 34 is inserted in the mounting hole 31*a* extending diagonally. The mounting hole 31*a* is inclined in a direction approaching toward the central axis 80 of the base member 31. Thus, the pin member 34 is mounted in a state of being inclined obliquely toward the central axis 80. Note that it may be configured such that the mounting hole 31*a* is in parallel to the central axis 80 and the pin member 34 has a shape bent obliquely.

The tip 34*a* of the pin member 34 is arranged at the position of the protrusion length 65 in the X1-direction from the lower surface of the base member 31. The tip 34*a* of the pin member 34 protrudes in the X1-direction than each of the tip 35 of the light-transmitting probe 32 and the tip 35 of the light-receiving probe 33 positioned at the first position 61. As shown in FIG. 6, each of the tip 35 of the light-transmitting probe 32 and the tip 35 of the light-receiving probe 33 is movable to the second position 62 protruding from the tip 34*a* of the pin member 34 in the X1-direction. In a state in which the plurality of pin members 34 are in contact with the head surface 91, the light-transmitting probe 32 and the light-receiving probe 33 are moved from the first position 61 toward the second position 62. With this, at the position between the first position 61 and the second position 62, each of the tip 35 of the light-transmitting probe 32 and the tip 35 of the light-receiving probe 33 comes into contact with the head surface 91.

(Arrangement of Pin Member and Probe)

As shown in FIG. 8, the plurality of pin members 34 are arranged side by side in the circumferential direction around the central axis 80 so as to surround the central axis 80 of the base member 31. With this, the plurality of pin members 34 is configured to lift hairs in the center side region 66 surrounded by the plurality of pin member 34 in accordance with the rotation of probe unit 30.

In the example of FIG. 8, the tips 34*a* of the plurality of pin members 34 are arranged side by side on the circumference 67 about the central axis 80 of the base member 31. In the example of FIG. 8, the plurality of pin members 34 is provided in a row on the circumference 67. In this embodiment, each of the tip 35 of the light-transmitting probe 32 and the tip 35 of the light-receiving probe 33 is positioned at the position on the circumference 67 or at the outer position proximate to the circumference 67. In the example of FIG. 8, an example is shown in which each of the tip 35 of the light-transmitting probe 32 and the tip 35 of the light-receiving probe 33 is arranged at the position on the circumference 67. Each of the tip 35 of the light-transmitting probe 32 and the tip 35 of the light-receiving probe 33 may be arranged at an outer position (e.g., see FIG. 13) proximate to the circumference 67.

Thus, in the example of FIG. 8, the tips 34a of the plurality of pin members 34, and each of the tip 35 of the light-transmitting probe 32 and the tip 35 of the light-receiving probe 33 are arranged so as to be aligned on the circumference 67. Then, in the circumferential direction about the central axis 80 of the base member 31, at least one of the plurality of pin members 34 is arranged between the adjacent light-transmitting probe 32 and light-receiving probe 33.

In the example of FIG. 8, the tips 35 of the two light-transmitting probes 32 and the tips 35 of the two light-receiving probes 33 are arranged at intervals of 90 degrees. The light-transmitting probe 32 and the light-receiving probe 33 are arranged alternately in the circumferential direction. In other words, the two light-transmitting probes 32 are arranged so as to face each other across the central axis 80, and the two light-receiving probes 33 are arranged so as to face each other across the central axis 80 in a direction perpendicular to a direction facing the two light-transmitting probe 32. With this, in the example of FIG. 8, between the light-transmitting probe 32 and the light-receiving probe 33 adjacent in the circumferential direction, four measurement channels 5 (measurement points) in total are formed.

Between the light-transmitting probe 32 and the light-receiving probe 33 adjacent in the circumferential direction, three pin members 34 are arranged. Twelve pin members 34 in total are provided such that three pin members 34 are arranged between adjacent probes of the four probes, respectively. In the example of FIG. 8, the tips 35 of the two light-transmitting probes 32, the tips 35 of the two light-receiving probes 33, and the tips 34a of the twelve pin members 34 are arranged at equal angular intervals on the circumference 67.

Thus, in the embodiment of FIG. 8, the light-transmitting probes 32, the light-receiving probes 33, and the pin members 34 are arranged at intervals in the circumferential direction. The hairs parted by the pin members 34 are moved into the area of the interval.

With such a configuration, the plurality of pin members 34 moves in the circumferential direction about the central axis 80 in accordance with the rotational movement of the base member 31 about the central axis 80. The moving path of the pin member 34 matches the circumference 67. As the pin member 34 is moved in the circumferential direction, the hairs of the head surface 91 are parted and lifted along the inclined surface of the pin member 34.

(Grip Portion)

As shown in FIG. 4, the probe unit 30 includes a grip portion 39 protruding from the base member 31 in the X2-direction opposite to the X1-direction. As shown in FIGS. 6 and 7, the light-transmitting probes 32, the light-receiving probes 33, the plurality of pin members 34, and the grip portion 39 are provided to the base member 31 so as to be rotated integrally with the base member 31. With this configuration, a subject 9 can rotate the entire probe unit 30 including the plurality of pin members 34 about the central axis 80 by gripping and rotating the grip portion 39 when performing the hair parting operation.

The grip portion 39 is arranged on the central axis 80 of the base member 31. At the center of the base member 31, a support column 39a extending in the X2-direction is provided. The grip portion 39 is fixed to the end of the support column 39a in the X2-direction. The grip portion 39 is formed in a circular shape and can be gripped and twisted (i.e., pivoted) by the subject 9. The grip portion 39 is positioned at the highest position protruding in the X2-direction in the probe unit 30.

(Probe Arrangement Procedures)

Figure 9:
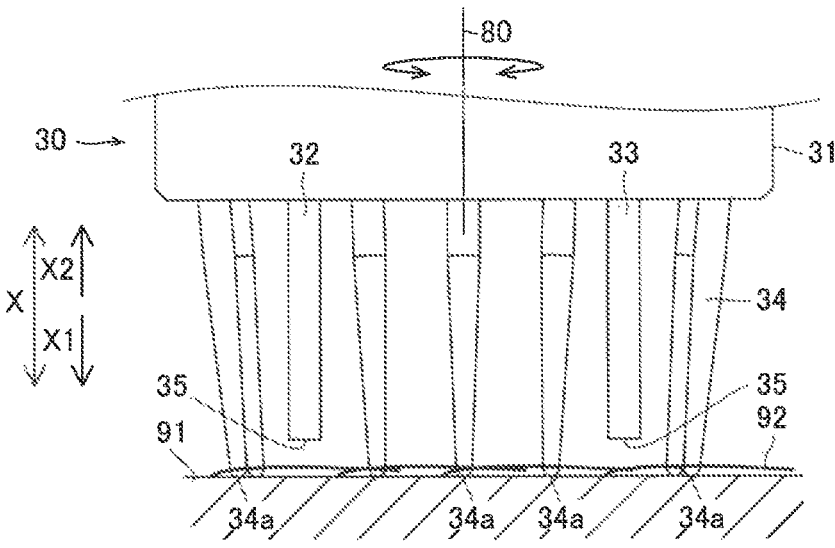
FIG. 9 is a schematic side view of a probe unit for explaining an arrangement operation of probes.
Figure 10:
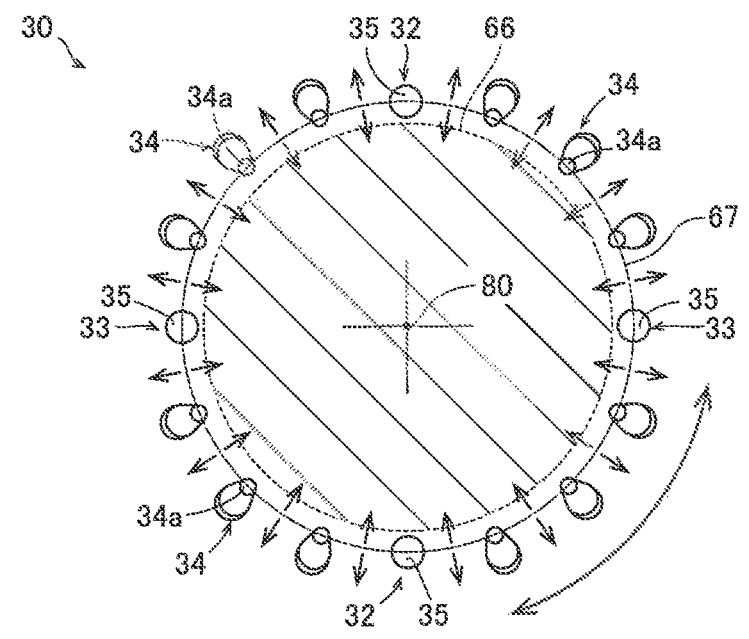
FIG. 10 is a schematic view showing a planar arrangement of pin members and probes for explaining the arrangement operation of the probes.
Figure 11:
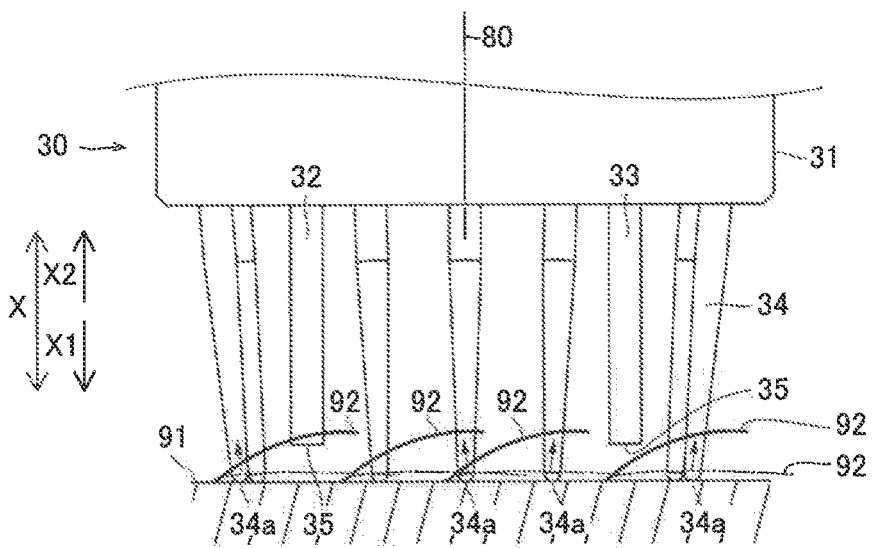
FIG. 11 is a schematic side view of a probe unit for explaining a lifting action of hairs by pin members.
Figure 12:
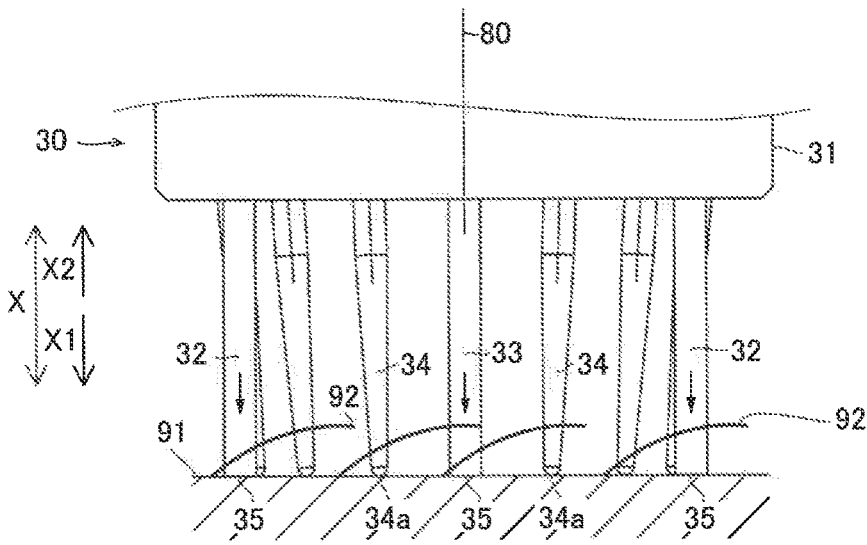
FIG. 12 is a schematic side view of a probe unit showing a state in which tips of probes are in contact with a head surface.

Referring now to FIGS. 9 to 12, the operation procedure for placing the light-transmitting probes 32 and the light-receiving probes 33 on the head surface 91 of the subject 9 will be described. All of the following operations can be performed by the subject 9 himself/herself and do not require the intervention of an assistant, such as, e.g., a doctor. Note that FIG. 9, FIG. 11, and FIG. 12 are schematic diagrams showing the probe unit 30 in a simplified manner and omit the illustration of the arrangement portion 55, the fiber head 42, etc.

First, the subject 9 (see FIG. 1) attaches the probe unit 30 to the holder 20. And the subject 9 attaches the holder 20 to the head. When the holder 20 is attached to the head, as shown in FIG. 9, the pin members 34 of the probe unit 30 come into contact with the head surface 91. At this time, it is acceptable that hairs are interposed between the tip 34a of the pin member 34 and the head surface 91. In FIG. 9, the hairs 92 of the subject 9 are schematically illustrated. The light-transmitting probes 32 and the light-receiving probes 33 are held at the first position 61 by the lock mechanisms 37 (see FIG. 6) and are positioned away from the head surface 91.

Next, the subject 9 rotates the probe unit 30 (base member 31) about the central axis 80 by gripping and rotating the grip portion 39 (see FIG. 4) of the probe unit 30. In accordance with the rotation of the probe unit 30, the plurality of pin members 34 is moved in the circumferential direction about the central axis 80 while contacting the head surface 91. As a result, as shown in FIG. 10, the pin members 34 move along the circumference 67 to part the hairs 92 inwardly and outwardly relative to the circumference 67. With the rotational movement about the central axis 80, the moving paths of the plurality of pin members 34 become closed circumference paths. Therefore, regardless of the direction in which the hairs 92 of the head surface 91 are orientated in FIG. 10, the hairs 92 are parted so as to be divided into the center side region 66 (hatched region) and the outer side region of the circumference 67.

As shown in FIG. 11, since the pin members 34 are inclined with respect to the head surface 91, the hairs 92 to be parted by the pin members 34 are lifted along the inclined pin members 34 after contacting the pin members 34. In practice, a plurality of hairs 92 is overlapped and generates frictional resistance to each other, and therefore hairs not in direct contact with the pin member 34 are also lifted. For this reason, the hairs 92 in the center side region 66 shown in FIG. 10 are entirely raised as a bundle. Due to the friction between the pin members 34 and the hairs 92 and the friction between the hairs 92, the hairs 92 in the center side region 66 remains lifted even if the subject 9 stops the rotation of the probe unit 30. When the hairs 92 are lifted up, the root portions thereof near the head surface 91 are raised. Therefore, a space suitable for placing the tip 35 of the probe is formed on the head surface 91 near the circumference 67 of the parted hairs.

In the state of FIG. 11, the subject 9 unlocks each of the four lock mechanisms 37 (see FIG. 6). That is, the subject 9 removes the spacer 58 from the shaft 51. Consequently, due to the biasing force of the biasing member 38 (see FIG. 6), as shown in FIG. 12, each of the tip 35 of the light-transmitting probe 32 and the tip 35 of the light-receiving probe 33 is moved from the first position 61 in the X1-direction and is brought into contact with the exposed head surface 91 on the circumference 67. In the state in which each of the tip 35 of the light-transmitting probe 32 and the tip 35 of the light-receiving probe 33 is in contact with the head surface 91, the biasing member 38 applies the pressing force toward the head surface 91 with respect to the probe to maintain the contact condition.

Consequently, the light-transmitting probe 32 and the light-receiving probe 33 are in close contact with the head surface 91. Thus, the preparation for measurement by the optical measurement device 100 is completed. Thereafter, when the operation input to start the measurement to the optical measurement device 100 is performed, the optical measurement device 100 starts the measurement of the cerebral function.

Note that the hardness of hairs 92 and the direction of hairs 92 (direction of the hair orientation) greatly differ depending on the individual difference of the subject 9 and the position at which the probe unit 30 is to be placed. In a case where hairs 92 are relatively hard and the roots of the hairs 92 are raised from the head surface 91, the head surface 91 is relatively easily exposed simply by parting the hairs 92. On the other hand, as shown in FIG. 9, in a case where the hairs 92 are relatively soft and the root portions of the hairs 92 are along the head surface 91 (hairs 92 is laying), it is difficult to part the hairs 92. In this case, the hairs 92 are likely to be interposed between the tip 35 of the probe and the head surface 91. The action of lifting the hairs 92 by the pin members 34 inclined as described above can lift the hairs 92 to raise the root portions of the hairs 92 in a case where the hairs 92 are along the head surface 91. Therefore, it is particularly effective.

Effects of this Embodiment

In this embodiment, the following effects can be obtained.

As described above, the optical measurement device 100 and the probe holder set 2 according to this embodiment is provided with the holder 20 to be mounted on the head of the subject 9 and the probe unit 30 held by the holder 20. The probe unit 30 includes the base member 31, the light-receiving probes 33, and the plurality of pin members 34. The base member 31 is held by the holder 20 in such a manner as to be rotatable about the central axis 80. The light-transmitting probe 32 protrudes from the base member 31 in the X1-direction toward the head surface 91. The light-receiving probe 33 protrudes from the base member 31 in the X1-direction. The plurality of pin members 34 protrude from the base member 31 in the X1-direction and parts the hairs 92 of the head surface 91. The plurality of pin members 34 is obliquely inclined at least either a direction toward the central axis 80 of the base member 31 or the circumferential direction about the central axis 80.

In this embodiment, by the above-described configuration, by simply arranging the probe unit 30 on the head surface 91 and rotating it by the subject 8 himself/herself, it is possible to rotate the pin members 34 to part the hairs 90.

At this time, the pin members 34 are obliquely inclined toward at least either a direction toward the central axis 80 or the circumferential direction. Therefore, by rotating the base member 31 in a state in which the pin members 34 are in contact with the head surface 91, it is possible to lift the hairs 92 along the slope of the pin member 34 while parting the hairs 92 even in a case where the hairs 92 extend along the head surface 91. As a result, the parted hairs 92 are raised so that a space in which the probe can be arranged without interposing the hairs 92 can be formed in the vicinity of the head surface 91. Also, the moving path of the pin member 34 is a closed circumference path about the central axis 80. Therefore, even in a case where the hairs 92 extend in any direction, it is possible to part the hairs 92 by the pin members 34. As a result, according to the optical measurement device and the probe holder set 2 of this embodiment, it is possible only by the subject to arrange the probe such that the hairs 92 are not interposed between the probe and the head surface 91 with a simple operation.

Further, in the above-described embodiment, with the above-described configuration, the following configuration can be obtained.

That is, in this embodiment, as described above, the plurality of pin members 34 is arranged side by side in the circumferential direction about the central axis 80 of the base member 31 so as to surround the central axis 80. The rotation of the probe unit 30 lifts the hairs 92 in the center side region 66 surrounded by the plurality of pin members 34. With this configuration, it is possible to lift the hairs 92 on the circumference trajectory along which the plurality of pin members 34 arranged in the circumferential direction moves and the hairs 92 inside the trajectory to thereby effectively raise the root portions of the hairs 92 in the center side region 66. Consequently, it is possible to expose the scalp surface covered by the hairs 92 to thereby more assuredly bring the tip of the probe (the light-transmitting probe 32, and the light-receiving probe 33) into close contact with the scalp surface.

In this embodiment, as described above, the tips 34a of the plurality of pin members 34 are arranged side by side on the circumference 67 about the central axis 80 of the base member 31. Each of the tip 35 of the light-transmitting probe 32 and the tip 35 of the light-receiving probe 33 is positioned at a position on the circumference 67 or at an outer position proximate to the circumference 67. With this configuration, the tips 34a of the plurality of pin members 34 move above the same circumference 67 in accordance with the rotation of the base member 31. Accordingly, it is possible to effectively obtain the action of parting the hairs 92 to the inside and the outside of the circumference 67 and the action of lifting the hairs 92 in the center side region 66 of the circumference 67, respectively. Then, each of the tip 35 of the light-transmitting probe 32 and the tip 35 of the light-receiving probe 33 is arranged on the circumference 67 or just outside the circumference 67. Therefore, it is possible to more effectively suppress the tip of the probe (the light-transmitting probe 32, the light-receiving probe 33) from pinching the hairs 92 in the vicinity of the outer peripheral edge of the bundle of the parted and lifted hairs 92.

Further, in this embodiment, as described above, each of the light-transmitting probe 32 and the light-receiving probe 33 is provided to the base member 31 so as to be movable to the first position 61 and the second position 62. The first position 61 is a position away from the head surface 91 than the plurality of pin members 34. The second position 62 is a position closer to the head surface 91 than the plurality of pin members 34. With this configuration, when the rotational operation for parting the hairs 92 by the plurality of pin members 34 is performed, each of the light-transmitting probe 32 and the light-receiving probe 33 is arranged at the first position 61. Therefore, it is possible to suppress the hairs 92 from being interposed between the tip of the probe and the scalp surface during the parting. It is possible to bring each of the light-transmitting probe 32 and the light-receiving probe 33 into close contact with the scalp surface by moving each of the light-transmitting probe 32 and the light-receiving probe 33 to the second position 62 after the scalp surface is exposed by the rotating operation of parting the hairs 92.

Further, in this embodiment, as described above, the probe unit 30 further includes the lock mechanism 37 and the biasing member 38 for each of the light-transmitting probe 32 and the light-receiving probe 33. The lock mechanism 37 releasably holds the probe at the first position 61. The biasing member 38 biases each of the light-transmitting probe 32 and the light-receiving probe 33 toward the second position 62. With this configuration, when the rotation operation for parting the hairs 92 is performed, each of the light-transmitting probe 32 and the light-receiving probe 33 can be held at the first position 61. Thus, after parting the hairs, it is possible to move each of the light-transmitting probe 32 and the light-receiving probe 33 to the second position 62 by simply unlocking the lock mechanism. Therefore, the operation for arranging the probe can be further simplified.

Further, in this embodiment, as described above, the probe unit 30 further includes the grip portion 39 protruding from the base member 31 in the X2-direction opposite to the X1-direction. The light-transmitting probes 32, the light-receiving probes 33, the plurality of pin members 34, and the grip portion 39 are provided to the base member 31 so as to be rotated integrally with the base member 31. With this configuration, it is possible to perform the parting of the hairs 92 by rotating the entire probe unit 30 with an extremely simple operation in which the subject 9 only grasps and rotates the grip portion 39. Further, for example, it is possible to avoid providing a complicated mechanism, such as, e.g., a mechanism in which only a plurality of pin members 34 is connected to the grip portion 39 to be rotatably moved with respect to the base member 31. Therefore, the configuration of the probe unit 30 can be simplified. As a result, the probe unit 30 can be miniaturized such that it can be easily mounted to the head of the subject 9.

Further, in this embodiment, as described above, at least one of the plurality of pin members 34 is arranged between the adjacent light-transmitting probe 32 and light-receiving probe 33 in the circumferential direction about the central axis 80 of the base member 31. With this configuration, the pin member 34 is arranged between the light-transmitting probe 32 and the light-receiving probe 33. For this reason, it is possible to reduce the rotation angle of the base member 31 to part the hairs 92 at the arrangement positions of the light-transmitting probe 32 and the light-receiving probe 33 by the pin members 34. For example, without rotating the base member 31 by one revolution, the base member 31 is rotated by at least the angular interval between the light-transmitting probe 32 and the light-receiving probe 33. With this, it is possible to part the hairs 92 at the arrangement position of the light-transmitting probe 32 and the light-receiving probe 33 by the pin members 34.

Further, in this embodiment, as described above, the light-transmitting probe 32 and the light-receiving probe 33 are detachably attached to the base member 31. With this configuration, it is possible to simplify the maintenance of the light-transmitting probe 32 and the light-receiving probe 33. Further, even in the case of replacing the light-transmitting probe 32 or the light-receiving probe 33 due to aging degradation, it is possible to replace only the probe without replacing the entire probe unit 30.

MODIFIED EMBODIMENTS

It should be understood that the embodiments disclosed here are examples in all respects and are not restrictive. The scope of the present invention is indicated by claims rather than by the above-described described descriptions of the embodiment and includes all modifications within the meanings and ranges equivalent to the claims.

For example, in the above-described embodiment, an example is shown in which the plurality of pin members 34 is arranged in the circumferential direction about the central axis 80 of the base member 31 so as to surround the central axis 80, but the present invention is not limited thereto. In the present invention, the plurality of pin members 34 may be arranged at radially displaced positions so as not to be aligned in the circumferential direction at the base member 31.

Further, in the above-described embodiment, an example is shown in which the tips 34a of the plurality of pin members 34 are arranged side by side on the circumference 67, but the present invention is not limited thereto. In the present invention, it is not required that all of the tips 34a of the plurality of pin members 34 are arranged on the circumference 67. Some of the tips 34a of the plurality of pin members 34 may be arranged at positions deviated from the circumference 67.

In the above-described embodiment, an example is shown in which the tips 34a of the plurality of pin members 34 are arranged in a line on the circumference 67, but the present invention is not limited thereto. In the present invention, the tips 34a of the plurality of pin members 34 may be arranged concentrically to form a plurality of rows.

Further, in the above-described embodiment, an example is shown in which each of the tip 35 of the light-transmitting probe 32 and the tip 35 of the light-receiving probe 33 is arranged at a position on the circumference 67, but the present invention is not limited thereto. As described above, each of the tip 35 of the light-transmitting probe 32 and the tip 35 of the light-receiving probe 33 may be arranged at an outer position proximate to the circumference 67. Other than the above, each tip 35 of the light-transmitting probe 32 and the light-receiving probe 33 may be arranged at an inner position proximate to the circumference 67. Each of the tip 35 of the light-transmitting probe 32 and the tip 35 of the light-receiving probe 33 is preferably provided in the vicinity of the path along which the pin member 34 moves in accordance with the rotation of the base member 31.

In the above-described embodiment, an example is shown in which each of the light-transmitting probe 32 and the light-receiving probe 33 is configured to be movable to the first position 61 and the second position 62, but the present invention is not limited thereto. In the present invention, each of the light-transmitting probe 32 and the light-receiving probe 33 may be fixed so as not to move in the X-direction with respect to the base member 31. In this instance, the plurality of pin members 34 may be configured to move in the X-direction. Further, the light-transmitting probes 32, the light-receiving probes 33, and the plurality of pin members 34 may be fixed so as not to move in the X-direction. In that case, each of the tip 35 of the light-transmitting probe 32 and the tip 35 of the light-receiving probe 33 may be provided so as to have the same protrusion amount as the tip 34a of the pin member 34.

Further, in the above-described embodiment, an example is shown in which the probe unit 30 is provided with the lock mechanism 37 and the biasing member 38, but the present invention is not limited thereto. In the present invention, it may be configured such that the subject 9 manually moves each probe without providing the lock mechanism 37 and the biasing member 38. Further, it may be configured to adapt the structure in which the holder 20 biases the probe unit 30 toward the head surface 91, instead of providing the biasing member 38.

Further, in the case of providing the lock mechanism 37, the lock mechanism 37 may be configured to releasably hold the probe by a structure other than the spacer 58. For example, the lock mechanism 37 includes a key member that engages a key groove formed in the shaft 51. For example, the lock mechanism 37 includes a ball plunger that releasably engages an engagement recess formed on the outer peripheral surface of the shaft 51. Thus, the configuration in which the lock mechanism releasably holds the probe is not limited to the one shown in the figure.

Further, in the above-described embodiment, an example is shown in which the grip portion 39 is provided to the probe unit 30, but the present invention is not limited thereto. In the present invention, the grip portion 39 may not be provided to the probe unit 30. The subject 9 may grasp and rotate any portion of the probe unit 30, and a dedicated grip portion for grasping may not be provided. However, considering that the subject 9 himself/herself operates the probe unit 30 mounted on the head, it is difficult to perform the operation of visually recognizing the probe unit 30 or adjusting the gripping position, and therefore, the operability can be remarkably improved by providing the grip portion 39.

Further, in the above-described embodiment, an example is shown in which the light-transmitting probes 32, the light-receiving probes 33, the plurality of pin members 34, and the grip portion 39 are provided to the base member 31 so as to be rotated integrally with the base member 31, but the present invention is not limited thereto. For example, it may be configured such that the portion of the base member 31 that holds the plurality of pin members 34 is relatively rotatable with respect to the portion that holds the light-transmitting probe 32 and the light-receiving probe 33. The probe unit 30 may be configured such that the plurality of pin members 34 rotates about the central axis 80 in a state in which the light-transmitting probe 32 and the light-receiving probe 33 are fixed.

Further, in the above-described embodiment, an example is shown in which three pin members 34 are arranged between the adjacent light-transmitting probe 32 and light-receiving probe 33 in the circumferential direction about the central axis 80 of the base member 31, but the present invention is not limited thereto. In the present invention, one, two, or four or more pin members 34 may be arranged between adjacent light-transmitting probe 32 and light-receiving probe 33. Further, as shown in FIG. 8, in a case where a plurality of pairs of the adjacent light-transmitting probe 32 and light-receiving probe 33 is provided, it may be configured such that a pin member 34 is not arranged between any one pair and that a pin member 34 is arranged between the other pair.

Further, in the above-described embodiment, an example is shown in which a total of twelve pin members 34 is provided to the base member 31, but the present invention is not limited thereto. The number of pin members 34 may be any number as long as it is plural. It is enough to provide a suitable number of pin members 34 to achieve an action of lifting the hairs 92 while parting the hairs 92 of the subject 9.

In the above-described embodiment, an example is shown in which two light-transmitting probes 32 and two light-receiving probes 33 are provided to the base member 31, but the present invention is not limited thereto. Any number of the light-transmitting probe 32 and the light-receiving probe 33 may be provided as long as at least one is provided. The number of the light-transmitting probes 32 and the number of the light-receiving probes 33 need not be the same, but may be different.

In the above-described embodiment, an example is shown in which the light-transmitting probe 32 and the light-receiving probe 33 are detachably attached to the base member 31, but the present invention is not limited thereto. In the present invention, the light-transmitting probe 32 and the light-receiving probe 33 may be provided inseparably with respect to the base member 31.

In the above-described embodiment, an example is shown in which the light-transmitting probe 32 and the light-receiving probe 33 have the L-shaped fiber head 42 and are attached to the notch arrangement portion 55 of the base member 31 from the side, but the present invention is not limited thereto. In the present invention, a straight fiber head may be provided instead of the L-shaped fiber head 42. In this instance, instead of the shaft 51 of the guide mechanism 36, a structure may be adopted in which a straight fiber head is inserted and mounted. The base member 31 may be provided with a through-hole through which, instead of the notch arrangement portion 55, a straight fiber head passes.

ASPECTS

It will be understood by those skilled in the art that the above-described exemplary embodiments are concrete examples of the following aspects.

(Item 1)

An optical measurement device comprising:

a device main body configured to irradiate a head surface of a subject with measurement light via a light-transmitting probe and detect the measurement light emitted from the head surface by way of an inside of a head via a light-receiving probe;

a holder configured to be attached to the head of the subject; and a probe unit held by the holder, wherein the probe unit includes:

a base member rotatably held by the holder about a central axis;

the light-transmitting probe protruding from the base member in a first direction toward the head surface;

the light-receiving probe protruding from the base member in the first direction; and a plurality of pin members each protruding from the base member in the first direction for parting hairs of the head surface, wherein the plurality of pin members is inclined obliquely at least either in a direction toward a central axis side of the base member or in a circumferential direction about the central axis.

(Item 2)

The optical measurement device as recited in the above-described Item 1, wherein the plurality of pin members is arranged side by side in the circumferential direction about the central axis of the base member so as to surround the central axis and is configured to lift the hairs in a center side region surrounded by the plurality of pin members in accordance with rotation of the probe unit.

(Item 3)

The optical measurement device as recited in the above-described Item 2, wherein tips of the plurality of pin members are arranged side by side on a circumference about the central axis of the base member, and wherein each of a tip of the light-transmitting probe and a tip of the light-receiving probe is arranged at a position on the circumference or at an outer position close to the circumference.

(Item 4)

The optical measurement device as recited in the above-described Item 1, wherein each of the light-transmitting probe and the light-receiving probe is provided to the base member so as to be movable between a first position away from the head surface than the plurality of pin members and a second position closer to the head surface than the plurality of pin members.

(Item 5)

The optical measurement device as recited in the above-described Item 4, wherein the probe unit further includes:

a lock mechanism configured to releasably hold each of the light-transmitting probe and the light-receiving probe at the first position; and a biasing member configured to bias each of the light-transmitting probe and the light-receiving probe toward the second position.

(Item 6)

The optical measurement device as recited in the above-described Item 1, wherein the probe unit further includes a grip portion protruding from the base member in a second direction opposite to the first direction, and wherein the light-transmitting probe, the light-receiving probe, the plurality of pin members, and the grip portion are provided to the base member so as to be rotated integrally with the base member.

(Item 7)

The optical measurement device as recited in the above-described Item 1, wherein in the circumferential direction about the central axis of the base member, at least one of the plurality of pin members is arranged between the light-transmitting probe and the light-receiving probe arranged adjacently.

(Item 8)

The optical measurement device as recited in the above-described Item 1, wherein the light-transmitting probe and the light-receiving probe are each detachably attached to the base member.

(Item 9)

A probe holder set for an optical measurement device configured to irradiate a head surface of a subject with measurement light via a light-transmitting probe and detect the measurement light emitted from the head surface by way of an inside of a head via a light-receiving probe, the probe holder set comprising:

a holder configured to be attached to the head of the subject; and a probe unit held by the holder, wherein the probe unit includes:

a base member rotatably held by the holder about a central axis:

the light-transmitting probe protruding from the base member in a first direction toward the head surface;

the light-receiving probe protruding from the base member in the first direction; and a plurality of pin members each protruding from the base member in the first direction for parting hairs of the head surface, and wherein the plurality of pin members is inclined obliquely at least either in a direction toward a central axis side of the base member or in a circumferential direction about the central axis.

DESCRIPTION OF SYMBOLS

1: Device main body
2: Probe holder set
9: Subject
20: Holder
30: Probe unit
31: Base member
32: Light-transmitting probe
33: Light-receiving probe
34: Pin member
34$a$: Tip (tip of the pin member)
35: Tip (tip of the light-transmitting probe and the light-receiving probe)
37: Lock mechanism
38: Biasing member
39: Grip portion
61: First position
62: Second position
66: Center side region
67: Circumference
80: Central axis
91: Head surface
92: Hairs
100: Optical measurement device
X1: Direction from a base member toward a head surface (first direction)
X2: Direction opposite to an X1-direction (second direction)

The invention claimed is:

1. An optical measurement device comprising:

a device main body configured to irradiate a head surface of a head of a subject with measurement light via a light-transmitting probe and detect the measurement light emitted from the head surface by way of an inside of the head via a light-receiving probe;

a holder configured to be attached to the head of the subject; and a probe unit held by the holder, wherein the probe unit includes:

a base member rotatably held by the holder about a central axis;

the light-transmitting probe protruding from the base member in a first direction toward the head surface;

the light-receiving probe protruding from the base member in the first direction; and a plurality of linear pin members, each protruding linearly from the base member in the first direction for parting hairs of the head surface, wherein a central axis line of each linear pin member of the plurality of linear pin members is inclined obliquely at least either in a direction toward a central axis of the base member or in a circumferential direction about the central axis.

2. The optical measurement device as recited in claim 1, wherein the plurality of linear pin members is arranged side by side in the circumferential direction about the central axis of the base member so as to surround the central axis and is configured to lift the hairs in a center side region surrounded by the plurality of linear pin members in accordance with rotation of the probe unit.

3. The optical measurement device as recited in claim 2, wherein tips of the plurality of linear pin members are arranged side by side on a circumference about the central axis of the base member, and wherein each of a tip of the light-transmitting probe and a tip of the light-receiving probe is arranged at a position on the circumference or at an outer position close to the circumference.

4. The optical measurement device as recited in claim 1, wherein each of the light-transmitting probe and the light-receiving probe is provided to the base member so as to be movable between a first position away from the head surface than the plurality of linear pin members and a second position closer to the head surface than the plurality of linear pin members.

5. The optical measurement device as recited in claim 4, wherein the probe unit further includes:

a lock mechanism configured to releasably hold each of the light-transmitting probe and the light-receiving probe at the first position; and a biasing member configured to bias each of the light-transmitting probe and the light-receiving probe toward the second position.

6. The optical measurement device as recited in claim 1, wherein the probe unit further includes a grip portion protruding from the base member in a second direction opposite to the first direction, and wherein the light-transmitting probe, the light-receiving probe, the plurality of linear pin members, and the grip portion are provided to the base member so as to be rotated integrally with the base member.

7. The optical measurement device as recited in claim 1, wherein in the circumferential direction about the central axis of the base member, at least one of the plurality of linear pin members is arranged between the light-transmitting probe and the light-receiving probe arranged adjacently.

8. The optical measurement device as recited in claim 1, wherein the light-transmitting probe and the light-receiving probe are each detachably attached to the base member.

9. A probe holder set for an optical measurement device comprising:

a holder configured to be attached to a head of a subject; and a probe unit held by the holder, wherein the probe unit includes:

a base member rotatably held by the holder about a central axis;

a light-transmitting probe protruding from the base member in a first direction toward a head surface of the head of the subject;

a light-receiving probe protruding from the base member in the first direction; and a plurality of linear pin members each protruding linearly from the base member in the first direction for parting hairs of the head surface, and wherein a central axis line of each linear pin member of the plurality of linear pin members is inclined obliquely at least either in a direction toward a central axis of the base member or in a circumferential direction about the central axis, and wherein the probe holder set is configured to irradiate the head surface of the subject with a measurement light via the light-transmitting probe and detect the measurement light emitted from the head surface by way of an inside of the head via the light-receiving probe.

10. The optical measurement device as recited in claim 1, wherein the central axis line of each linear pin member of the plurality of linear pin members is inclined obliquely at an inclination angle $\theta$ between 1 degree and 10 degrees with respect to the central axis.

11. The optical measurement device as recited in claim 1, wherein each linear pin member of the plurality of linear pin members has a tapered tip.

12. The probe holder set for an optical measurement device as recited in claim 9, wherein the central axis line of each linear pin member of the plurality of linear pin members is inclined obliquely at an inclination angle $\theta$ between 1 degree and 10 degrees with respect to the central axis.

13. The probe holder set for an optical measurement device as recited in claim 9, wherein each linear pin member of the plurality of linear pin members has a tapered tip.

* * * * *